United States Patent [19]

MacFarlane et al.

[11] Patent Number: 5,313,267
[45] Date of Patent: May 17, 1994

[54] METHOD AND INSTRUMENT FOR SELECTING PERSONAL COMPATIBLE COLORS

[75] Inventors: Darby S. MacFarlane; David K. MacFarlane, both of Hastings On Hudson; Fred W. Billmeyer, Schenectady, all of N.Y.

[73] Assignee: Chromatics Color Sciences International Inc., Hastings on Hudson, N.Y.

[21] Appl. No.: 21,657

[22] Filed: Feb. 22, 1993

Related U.S. Application Data

[63] Continuation of Ser. No. 818,448, Dec. 30, 1991, abandoned, which is a continuation of Ser. No. 402,815, Aug. 24, 1989, abandoned, which is a continuation-in-part of Ser. No. 306,286, Feb. 2, 1989, abandoned, which is a continuation of Ser. No. 204,938, Jun. 6, 1988, abandoned, which is a continuation of Ser. No. 904,369, Sep. 8, 1986, abandoned, which is a continuation-in-part of Ser. No. 833,661, Feb. 21, 1986, abandoned, which is a continuation of Ser. No. 514,618, Jul. 18, 1983, abandoned.

[51] Int. Cl.$^5$ .............................. G01J 3/50; G01J 3/52
[52] U.S. Cl. .................................... 356/405; 356/421; 364/526; 434/99; 434/100
[58] Field of Search .............. 356/402, 405, 406, 407, 356/416, 418, 419, 421, 422, 423, 424, 425, 243; 364/498, 526, 413; 434/98, 99, 100

[56] References Cited

U.S. PATENT DOCUMENTS

| | | | |
|---|---|---|---|
| 1,582,122 | 4/1926 | Clapp | 356/423 |
| 3,003,388 | 10/1961 | Hunter et al. | 356/405 |
| 4,241,738 | 12/1980 | Lübbers et al. | 356/40 |
| 4,561,850 | 12/1985 | Fabbri et al. | 434/100 |
| 4,654,794 | 3/1987 | O'Brien | 364/413 |
| 4,681,546 | 7/1987 | Hart | 356/419 |
| 4,909,632 | 3/1990 | McFarlane | 356/421 |

FOREIGN PATENT DOCUMENTS

0257328  12/1985  Japan ................... 356/406

OTHER PUBLICATIONS

Jackson, *Color Me Beautiful*, New York, Ballantine Books Apr. 1981, pp. 25, 26, color palettes, 37–39, 41–59, 61–74, 143–147.

Pinckney et al, *Your New Image Through Color & Line*, California Fashion Image/Crown Summit Books, Sep. 1981, pp. 1–3, 17, 21–29, 97–105, 111, 112, 120–127.

Ralph M. Evans, "Human Skin," in Ralph M. Evans, An Introduction to Color, Wiley, New York, 1948, pp. 87–90.

C. S. McCamy, H. Marcus, and J. G. Davidson, A Color-Rendition Chart, J. Appl. Photogr. Eng. 2, 95–99 (1976).

C. A. Pearson, Face Colour as a Sign of Tuberculosis, Color Res. Appl. 7, 31–33 (1982).

P. A. Lovett and M. B. Halstead, "Measurement of the Skin Colour of Babies in Hospital" in Proc. CIBS Lighting Conference, 1986, HMSO, London, 1986, pp. 140–154.

Günter Wyszecki and W. S. Stiles, "Color Science", 2nd Edition Wiley, New York, p. 63.

*Primary Examiner*—F. L. Evans
*Attorney, Agent, or Firm*—Brumbaugh, Graves, Donohue & Raymond

[57] ABSTRACT

Skin coloration categories are identified based upon blue and yellow undertones of the skin using a color measuring device, developing the Hunter b value, utilizing that value alone to determine which of several categories of skin coloration a subject's skin exhibits. Category selection is made by comparison of measured Hunter b with ranges of Hunter b value of skin color categories. Instrumentation to effect the method includes the color measuring device, a central processing unit (CPU), memory storing the ranges of Hunter b, and an output device such as a printer, LCD, or CRT. The skin color Hunter b is calculated and compared to stored ranges to assign a category. The output device displays the category of skin color based upon the central processing unit's comparison. Colors compatible with skin color categories are identified or formulated based upon broad color family designation, yellow, brown, red, etc., and a comparison of measured and stored ranges of known or specially developed color characteristics for the particular family.

87 Claims, 3 Drawing Sheets

METHOD AND INSTRUMENT FOR SELECTING PERSONAL COMPATIBLE COLORS

This application is a continuation of application Ser. No. 07/818,448, filed on Dec. 30, 1991, now abandoned, which is a continuation of Ser. No. 402,815, filed on Aug. 24, 1989, now abandoned, which is a continuation-in-part of Ser. No. 306,286, filed Feb. 2, 1989, now abandoned which is a continuation of Ser. No. 204,938, filed Jun. 6, 1988, now abandoned which is a continuation of Ser. No. 904,369, now abandoned, filed Sep. 8, 1986, now abandoned, which is a continuation-in-part of Ser. No. 833,661, filed Feb. 21, 1986, now abandoned, which is a continuation of Ser. No. 514,618, filed Jul. 18, 1983, now abandoned.

BACKGROUND OF THE INVENTION

This invention relates to a method and instrument for identifying categories of skin coloration for compatibility with colors of clothing, makeup, etc., and more particularly to methods and apparatus for classifying skin color based upon its blue and yellow undertones and for assigning one of a plurality of basic categories for which compatible colors have been selected.

Recently, numerous proposals for identifying colors of, for example, clothing, makeup, hair colorants, and the like, based upon an individual person's coloration have been put forth. Some of these proposed techniques have taken into account the color of the person's complexion, but have incorrectly emphasized redness and have also wrongly relied upon eye color, color of hair, and even racial background to assign color categories to the person. Based on that assignment a preselected collection of colors of fabric or other materials was chosen.

Draping techniques, whereby drapes of a series of colors are placed adjacent an individual's face for an assessment of compatibility, have been in widespread use. The purpose has been to better enable the evaluated individual to choose clothing and other items of a harmonious color. These draping techniques have had some success. Being subjective, they depend, however, upon the observational skills of the one who conducts the assessment and cannot be relied upon for consistent accuracy.

Much has been written about the various color assessment techniques. Often this has been misleading in that the true scientific basis for skin color categorization was not perceived. Again, for example, writings on the subject have advised attention to eye color, hair color, or race, or have suggested assessment of the redness or pallor of the subject individual. Although blue and yellow have been mentioned along with other colors and/or features said to contribute to an assessment of compatible colors, there have been only vague mentions of these broad color families encompassing many different colors in the blue and yellow families. There has not been any clear expression of exact blues or yellows contributing to the proposed assessments. Nor has there been any exact specification of a reproducible parameter derived from these colors and capable of accurate, consistent use in skin color assessment.

Several attempts have been made to quantify color assessment and, after long, hard work on the subject, these attempts have failed. It has been generally recognized by those who have considered the possibility that a consistent, scientifically sound, and reproducible technique for accurately categorizing an individual's skin coloration would be extremely desirable as would the availability of an instrument for consistently and accurately assessing and categorizing skin color. Prior to the subject invention, there has never been a correlation of physically measured color characteristics with perceived categories of skin color. Neither has any skin color parameter been identified that enables consistent categorization for the purposes described. The reliable coloration of products for compatibility with skin color has been unknown, as well.

In color identification utilized in other endeavors, numerous qualities, measurable values, or parameters exist. To identify color accurately more than one characteristic, and often three values, are used. No single value satisfactorily defines color.

Although extensive collections of colors of non-skin objects, particularly fabrics, for each skin color category have been determined visually, there remains a need to quickly and reliably identify new colors as compatible with one or more skin color categories. Prior to this invention, no color characteristics have been identified or developed to permit this.

BRIEF SUMMARY OF THE INVENTION

By this invention skin coloration is accurately measured in a consistent, repeatable fashion on the basis of blue and yellow undertones in any person's skin color, utilizing a known color evaluation device and calculating a single parameter dependent on the blue and yellow content. Recognition of skin color exclusively as the determinative factor in arriving at personal color categorization, then the further recognition of the blue and yellow undertones as the controlling characteristic, to the exclusion of other color measurements, contrary to the popular techniques and writings, were significant steps toward the establishment of a scientifically sound and readily reproducible personal color assessment method.

In the method according to the invention, a color measuring device is used to develop the necessary measurements to calculate the Hunter b value. That calculation is effected, and the value thus determined is compared with preselected ranges of this b value that have been established empirically on the basis of analyses of thousands of test subjects to arrive at one of several categories of skin coloration corresponding to one of the preselected b value ranges. The instrument according to the invention incorporates the color measuring device, a microprocessor or other central processing unit (CPU), and memory storing the preselected ranges of b values that correspond to skin color categories. The central processing unit calculates the Hunter b value using the color coordinates or values measured by the measuring device. The CPU then compares the derived Hunter b value with the stored ranges to produce an output indicative of a particular category. In the embodiment of the method and apparatus according to the invention that is described herein specifically, the categories are four in number and preselected colors of fabric, cosmetics, hair colorants, and the like are assigned to each based upon its predetermined harmonious or aesthetically pleasing appearance when used in relation to a skin color in the particular category. The invention can be practiced with many more or fewer categories of skin color. As the invention is practiced with more numerous skin color categories, very narrow ranges of skin coloration can be identified as compatible with products of a particular color.

The Hunter b value utilized to arrive at skin color categories that are repeatable and useful in determining compatible colors of associated fabrics and the like is one of three Hunter values, L, a, and b. Like other sets of color values, these are used, always in conjunction with one another, to define a color. Many other color character defining coordinates and values are known and are in use. These have been evaluated in the attempt to identify or develop a measurement or calculated value that will enable competent, reproducible, and scientifically valid assignment of categories. For example, the tristimulus colorimeter is used as the color measuring device in preferred embodiments of the method and instrument according to this invention. Starting with the measured standard CIE (Commission Internationale de l'Éclairage) tristimulus values X, Y and Z, certain colorimeters that are commercially available devices, with some computation capacity of their own, produce three well known coordinates, Y, x and y. These are standard color measurements established by the CIE and adopted by the ASTM (American Society for Testing and Materials). Neither the three tristimulus values X, Y and Z nor the additionally produced x an y values, alone or in combination, will suffice to permit acceptable categorization of skin color in the desired manner. Either set of three values, X, Y and Z, or Y, x and y, are, however, adequate to permit calculation of the Hunter b value. Certain commercial colorimeters are equipped with sufficient calculating capacity to develop the Hunter values L, a and b. If not, then the calculation of b is effected by the CPU of the invention. It is only necessary that an instrument be capable of measuring the values required to calculate the Hunter b value.

In a preferred practice of the method according to the invention, multiple tristimulus colorimeter readings are taken and averaged by the CPU for a more accurate Hunter b value calculation. Typically, an individual person's cheek, free of makeup, is the site of the measurement. However, the back of the person's hand or another area can be measured, but some shifting of the categories then may result. For example, when the back of the hand is the measurement site, the presence and clear visibility of numerous blood vessels shifts the ranges of Hunter b values that correspond to the skin color categories.

Good repeatability has been demonstrated by the skin color category identifying method and instrument of this invention and the category determination is made without resorting to eye color, hair color, or race. Insofar as race is concerned, the methods and apparatus of the invention have established among black people tested a wide range of colors, in all of the categories of skin color described herein. This is completely contrary to prior writings erroneously assigning black subjects to a single, subjective category and clearly evidencing a lack of recognition of the color characteristics distinguishing individuals.

In short, the recognition of the single measurable quantity, Hunter b, as the distinguishing feature on which skin color differentiation could be based departed significantly from the ordinary color identification on the basis of several parameters and departed entirely from any earlier approach to skin color classification.

Extensive collections of fabric colors, called swatch packs, have been assembled that are compatible with the skin color categories. Determination of the color defining features that establish compatible colors is not as straightforward as the precise measurement of skin color category discussed above. For fabrics and other non-skin matter other than cosmetics, the color characteristics that appear to determine whether or not a particular non-skin color will be compatible with a particular skin color category vary from one color family to another. By "color family" is meant the broad designation of color, e.g., yellow, red, blue, green and so on. The Hunter b value appears to be determinative of categories of compatibility for the color families yellow, gold, orange, red and white. Three new characteristics, Hunter hue angle $h_H$, Hunter chroma $C_H$, and Hunter saturation $s_H$, were developed for and appear to work satisfactorily for identifying compatible categories from the color families beige, brown, pink, purple, blue, green, grey and black. These developed characteristics are used alone, together with Hunter b, in combination, or with the Hunter lightness value L to sort these families into colors that are identified with the skin color categories with which they are compatible.

Cosmetic colors differ from other non-skin matter in their skin color compatibility characteristics. In cosmetics, particular colors in the various color families can be categorized for skin color compatibility based on their Hunter b values. However, with some color families only two ranges of this characteristic can be identified, and with other families overlapping of the ranges is necessary to accommodate varying degrees of skin darkness. Beige and brown foundation cosmetics need to take into account skin darkness as well as the yellow and blue content and a system for achieving this is presented below.

The color characteristics of non-skin matter that establish compatibility categories of skin coloration can also be used to formulate new colors for products such as cosmetics, fabrics, etc. By altering the content of standard blue or yellow coloring agents such as dyes, pigments or other colorants, the color of non-skin matter can be adjusted to be compatible with a desired skin color category. This is done by altering the formulation sufficiently for an item or substance of a particular color family to bring the relevant characteristic or characteristic into a range previously identified as defining colors of that family compatible with the desired skin color category, without changing other characteristics of the color.

The above and further advantages of this invention will be better understood with reference to the following detailed description of the preferred embodiments taken in combination with the attached drawings.

DETAILED DESCRIPTION OF THE PREFERRED EMBODIMENTS

Figure 1:
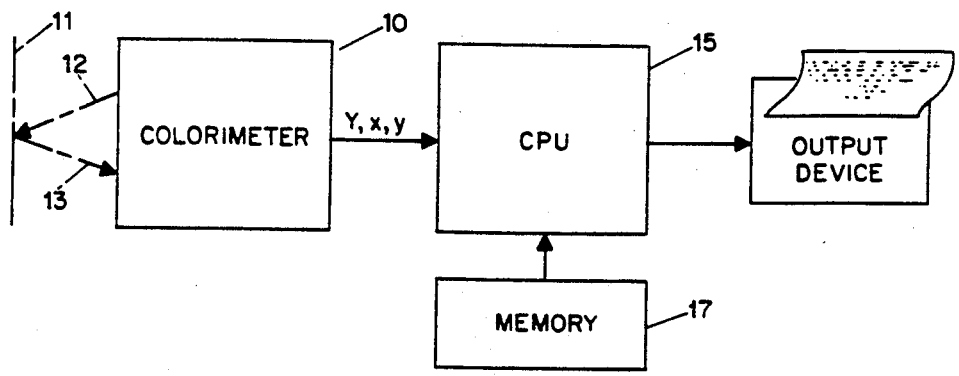
FIG. 1 is a block diagram illustration of an instrument for determining Hunter b value based on tristimulus colorimeter development of Y, x, y and determination of one of several skin coloration categories having b value ranges held in memory.

Any modern version of two general types of color-measuring instruments is suitable for the skin color measurement according to this invention. The basic components of either type of instrument are a light source, a sample illumination and viewing arrangement, a means of selecting certain wavelengths of light for the measurement, a detector of the light reflected from the sample, and some relatively simple computing capacity. The main purposes of the computing capacity are to store and apply calibration information and to calculate various color coordinates for later use. In FIG. 1, a color measuring instrument 10 is illustrated. An individual person's skin 11 is illuminated by the instrument as generally indicated by the broken line arrow 12 and the instrument receives illumination reflected from the skin 11 as generally indicated by the broken line arrow 13. Based on the illumination received by reflection from the skin the instrument 10 develops the coordinates Y, x and y. In FIG. 1 the instrument 10 is a colorimeter, commercially available and suitable for development of the values Y, x, and y.

Alternatively, the other type of instrument that can be used in the skin color categorization method according to this invention is the spectrophotometer that derives tristimulus values, from which can be computed the color values used to establish category of skin color as discussed below Important to the use of a commercial colorimeter of the kind employed for the color measurement instrument 10 of FIG. 1 is the calibration of the instrument using a standard. In the early development of this application, the "Light Skin" sample from the Macbeth Color Checker, described in the publication of C. S. McCamy, H. Marcus, and J. G. Davidson, "A Color-Rendition Chart," J. Appl. Photogr. Eng. 2, 95–99 (1976) was used. A tile of this approximate color was selected for its greater durability as an instrument standard. It was found, however, that the use of the "Light Skin" painted paper as the primary standard did not adequately avoid the phenomenon known as metamerism, by which objects that look alike (have the same perceived color) under some kinds of light sources or to some observers do not match under other types of light sources or to other observers. By this phenomenon colorimeters may not read their colors the same as the average human observer would under the daylight type light source usually employed for visual observation, hence leading to an error in colorimeter calibration.

As an improved primary standard, the skin of a subject whose skin color measurements were highly reproducible and in the approximate center of the range of skin colors of the human population was selected. The spectral reflectance factors of the skin of this subject were carefully measured on a Macbeth 1500 Plus spectrophotometer (Macbeth, Newburgh, N.Y.); these data are given in column 2 of Table II at the wavelengths listed in column 1. By using well-established techniques of computer color matching, carried out on an ACS 1800 system equipped with an ACS SpectroSensor II color measuring instrument (Applied Color Systems, Princeton, N.J.) a colorant formulation matching this skin color was developed. The spectral reflectance factors for this match are given in column 3 of Table II. It may be seen that the data closely match those of column 2, indicating the absence of metamerism. Calculations according to the CIE 1976 CIELAB system showed that the two data sets match to within 0.27–0.36 units, less than can be perceived by human color vision, for daylight, incandescent light, and cool white fluorescent light, the three most commonly used light sources for the proposed applications.

The above-mentioned formulation was made up in a stable, durable material, and tiles were prepared as instrument standards. The spectral reflectance factors of one of these tiles are given in column 4 of Table II. It was found, however, that the improvement in calibration resulted in color coordinates that were significantly different from those obtained in the many studies made with the earlier system. A decision was made to adjust the calibration values of the new tiles in order to achieve consistent results between the new and old methods of calibration. Column 5 of Table II gives the adjusted set of spectral reflectance factors for the tile of column 4. The CIE and Hunter color coordinates, for measurement with the specular component excluded and calculated for CIE standard illuminant C and the 1931 2° CIE standard observer, are also tabulated for each of the samples in the table.

With a suitable standard, basically, calibration is carried out by forcing the colorimeter 10 to give the desired color coordinates Y, x and y mentioned above, while utilizing the colorimeter with the standard tile chosen. The method of calibration is known for particular instruments and follows a series of steps prescribed by the manufacturer that need not be detailed here.

With the instrument correctly calibrated, the measuring head or instrument orifice is placed against the specimen to be measured. In a preferred approach, the instrument head is pressed against the makeup-free cheek of the individual person whose skin coloration is to be assessed. In a colorimeter of the type shown in FIG. 1 at block 10 the instrument has an internal microprocessor or other computing capability so that it is able to develop the color coordinates Y, x and y from the measured values X, Y and Z (Y being the same in each case). Certain colorimeters develop the Hunter color coordinates L, a, b, of which the coordinate b figures prominently in the skin color categorization of the invention as explained below. Since the degree of computation that the color measuring device 10 (i.e. colorimeter or spectrophotometer) internally performs varies, the manner of calculating the Hunter values from the tristimulus coordinates is useful to an understanding and practice of the invention and will enable correct use of a CPU by appropriate calculation to perform the invention with any commercially available colorimeter or spectrophotometer. Most modern color measuring instruments begin with measurement of the tristimulus values X, Y, and Z. From these can be derived the CIE chromaticity coordinates x and y:

$$x = X/(X+Y+Z) \tag{1}$$

$$y = Y/(X+Y+Z) \quad (2)$$

The instrument 10 of FIG. 1 outputs the triplet of values x, y and Y as the starting point for further calculations by a central processing unit which can be a microprocessor or personal computer 15. The remaining two tristimulus values X and Z are available by computation as follows:

$$X = xY/y, \text{ and} \quad (3)$$

$$Z = (1-x-y)Y/y \quad (4)$$

The CPU can thus develop the Hunter value b discovered in accordance with this invention to be the most useful color coordinate for describing categories of skin colors. The Hunter value is one of three values derived by Richard S. Hunter in 1958. Richard S. Hunter, "Photoelectric Color Difference Meter", J. Opt. Soc. Am. 48, 985–995 (1958). The equations for these are:

$$L = 10 \, (Y)^{\frac{1}{2}} \quad (5)$$

$$a = 17.5 \, (1.02 \, X - Y)/Y^{\frac{1}{2}} \quad (6)$$

$$b = 7.0 \, (Y - 0.847 \, Z)/Y^{\frac{1}{2}} \quad (7)$$

where L is a lightness coordinate whose values correlate better with the visual perceptions of the lightness of object colors than do values of Y; a is a coordinate denoting redness or greenness, for which positive values denote that the color is red rather than green, and negative values the opposite; and b is a yellowness-blueness coordinate, for which positive values denote that the color is yellow rather than blue, and negative values the opposite. For yellow colors, starting with $a = b = 0$ and an appropriate high value of L, which would be a light grey, increasing positive values of b result in a series of colors that may be described as light yellowish grey, pale yellow, light yellow, brilliant yellow, and vivid yellow, in turn. Thus b is a measure of the "intensity" of the yellow color.

Ordinarily, all three Hunter values are utilized to describe a color. However, for the purpose of skin color categorization, particularly as used to identify categories of skin coloration compatible with previously identified series of colors as may be useful in selecting clothing and the like, it was discovered by the inventor that the Hunter value b alone was most useful to provide a reliable measure of the categories of skin coloration best suited to that endeavor. The coordinate b provides a reliable measure of the yellow undertone of the color of human skin. It should be pointed out that other measures of the yellowness of colors, including those standardized by the CIE, namely, b*, v, and v*, and by the ASTM, including the Yellowness Index of Method D 1925, are not satisfactory in the same way as Hunter b for the purposes stated above. Thus, in the particular arrangement of FIG. 1, wherein the colorimeter 10 produces the values Y, x, y, the computer 15 derives the Hunter value b. Clearly, development of Hunter b, for use in this invention can be accomplished by an instrument that measures just the required variables Y and Z of equation (7).

Y is a function, well known in the science of color, that measures the yellow content, as well as the lightness, of a color. It has maximum weighting in the yellow to red region of the spectrum (i.e., the region extending from the green side of purest yellow in the spectrum into red). Z is a function, also well known in the science of color, that measures the blue content of the color, with maximum weighting in the blue region of the spectrum. Together these factors, or others like them, can be used to calculate a yellow-blue factor as typified by equation (7) defining Hunter's b.

The equations (5) and (7) make it clear that Hunter's b is not independent of lightness. L, the Hunter lightness coordinate, is 10 (Y and is a measure of the lightness of color, i.e., luminous reflectance. Hunter's b is weighted by this coordinate, as follows:

$$b = \frac{7.0 \, (Y - 0.847Z)}{Y^{\frac{1}{2}}} \quad (7)$$

$$b = \frac{70 \, (Y - 0.847Z)}{10 Y^{\frac{1}{2}}}, \text{ or}$$

$$b = \frac{70 \, (Y - 0.847Z)}{L}.$$

So the Hunter value b can be described as a yellow-blue factor consisting of the difference between (1) a function measuring the yellow content of the color and (2) a function measuring the blue content of the color, the difference being suitably weighted by (3) a term that is a function of the lightness (luminous reflectance) of the color, the function measuring the yellow content having maximum weighting in what is substantially the yellow to red region of the spectrum and the function measuring the blue content of the color having maximum weighting in what is substantially the blue region of the spectrum.

Figure 2:
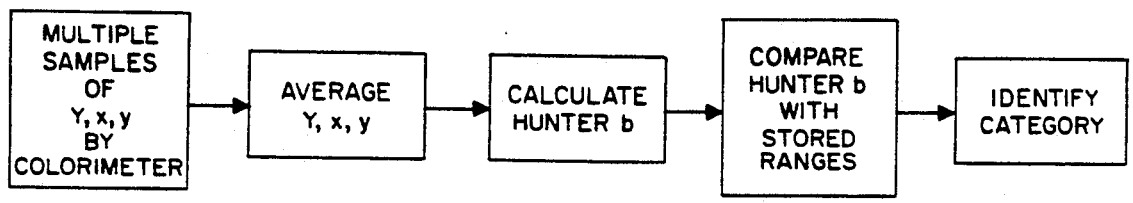
FIG. 2 is a schematic illustration in block diagram form illustrating the steps in the method of arriving at skin color category.
Figure 3:
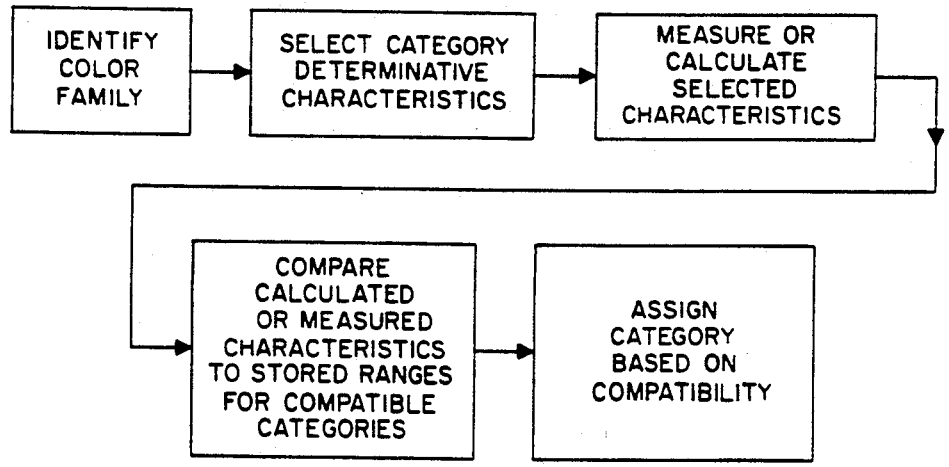
FIG. 3 is a schematic illustration in block diagram form illustrating the steps in the method of arriving at compatibility with skin color category or categories of the color of non-skin objects.

For greater accuracy, multiple Y, x and y readings can be made with the colorimeter 10 as suggested in the steps of the method outlined in FIG. 2, in which case the computer 15 simply averages the values Y, x, y for greater accuracy in the calculation of b. With the b value of the color of the skin 11 now available, the CPU 15 compares that with predetermined ranges of b values empirically identified with categories of skin coloration and stored in memory 17. This division of the total range of b values into individual ranges that define skin color categories was quite different from the use of multiple values to define color and proved surprisingly repeatable and accurate. Assignments of category based on measurement and b value calculation agree with visual assessments. The ranges of b values corresponding to, for example, four skin color categories are stored in the memory 17. For cheek measurement, based on assessments of thousands of individuals, the boundaries between the four ranges appear to be at substantially 11.2, 12.7 and 14.3.

Some shifting of the ranges of b value occurs in dependence on the location of the skin where assessment occurs. For example, utilizing the back of the subject's hand, boundaries between the exemplary four ranges appear to occur at 9.8, 11.0 and 12.1. This is believed to be a function of the number and visibility of blood vessels at that location. In either case the lowermost range, that of category I, consists of b values below the lowest boundary value. The next higher range, that of category II, is between that lowest boundary value and the next higher boundary value, which is the middle value. The next range, that of category III, is from the middle value to the highest boundary value, and the fourth and highest range, that of category IV, consists of all b values above the highest dividing value.

As for the assignment of particular colors of fabric and the like to categories compatible with the four skin color categories, the following colors, identified by CIE Y, x, y values have been identified and categorized. In the following tabulation of fabric colors, color category I is the category compatible with skin category I, corresponding to the lowest Hunter b value range of skin measurement (i.e. below about 11.2, cheek measurement), color category II represents compatibility with the next higher skin color category II (from about 11.2 to 12.7, cheek measurement), color category III represents colors compatible with the next higher category of skin color, category III (about 12.7 to 14.3, cheek measurement), and color category IV represents compatibility with the highest category IV of skin color (above about 14.3, cheek measurement).

TABLE I

| Y | x | y | Category |
|---|---|---|---|
| Yellow Color Family | | | |
| 71.2 | 0.339 | 0.363 | I |
| 73.8 | 0.344 | 0.375 | II |
| 71.6 | 0.386 | 0.433 | III |
| 60.5 | 0.441 | 0.465 | IV |
| 30.9 | 0.481 | 0.438 | III |
| 23.5 | 0.471 | 0.410 | III |
| Orange Color Family | | | |
| 22.7 | 0.543 | 0.367 | III |
| 46.1 | 0.443 | 0.407 | IV |
| 42.9 | 0.438 | 0.404 | IV |
| 31.1 | 0.491 | 0.415 | IV |
| 33.6 | 0.544 | 0.402 | IV |
| 14.2 | 0.520 | 0.362 | III |
| 9.9 | 0.481 | 0.366 | III |
| 24.9 | 0.529 | 0.364 | III |
| Red Color Family | | | |
| 8.0 | 0.495 | 0.297 | I |
| 7.3 | 0.526 | 0.304 | II |
| 20.2 | 0.429 | 0.327 | II |
| 9.6 | 0.451 | 0.284 | I |
| 5.0 | 0.460 | 0.294 | I |
| 3.6 | 0.469 | 0.302 | I |
| 45.3 | 0.574 | 0.344 | IV |
| 13.9 | 0.554 | 0.335 | III |
| 11.4 | 0.567 | 0.328 | III |
| 17.0 | 0.575 | 0.344 | IV |
| Beige Color Family | | | |
| 57.2 | 0.376 | 0.390 | IV |
| 43.7 | 0.370 | 0.380 | IV |
| 54.0 | 0.364 | 0.377 | IV |
| 57.2 | 0.378 | 0.391 | IV |
| 55.6 | 0.358 | 0.372 | III |
| 31.8 | 0.370 | 0.380 | IV |
| 37.2 | 0.361 | 0.377 | IV |
| 56.9 | 0.348 | 0.359 | II |
| Brown Color Family | | | |
| 2.3 | 0.355 | 0.325 | I |
| 20.3 | 0.354 | 0.351 | II |
| 5.8 | 0.359 | 0.345 | II |
| 7.6 | 0.362 | 0.350 | II |
| 39.6 | 0.396 | 0.386 | IV |
| 21.9 | 0.391 | 0.374 | IV |
| 22.3 | 0.402 | 0.385 | IV |
| 4.5 | 0.394 | 0.349 | II |
| 4.0 | 0.420 | 0.351 | II |
| 7.5 | 0.402 | 0.371 | II |
| Pink Color Family | | | |
| 43.7 | 0.393 | 0.285 | I |
| 22.7 | 0.437 | 0.288 | I |
| 19.8 | 0.422 | 0.283 | I |
| 14.0 | 0.381 | 0.319 | II |
| 33.8 | 0.363 | 0.333 | II |
| 57.8 | 0.357 | 0.302 | II |

TABLE I-continued

| Y | x | y | Category |
|---|---|---|---|
| 47.6 | 0.369 | 0.313 | II |
| 25.7 | 0.384 | 0.302 | II |
| 38.3 | 0.355 | 0.314 | II |
| 9.2 | 0.433 | 0.256 | I |
| 26.9 | 0.374 | 0.332 | II |
| 41.4 | 0.465 | 0.380 | IV |
| 44.9 | 0.408 | 0.350 | III |
| 45.2 | 0.393 | 0.366 | IV |
| 47.4 | 0.383 | 0.375 | IV |
| 26.0 | 0.463 | 0.341 | III |
| 37.3 | 0.419 | 0.381 | IV |
| 23.7 | 0.473 | 0.359 | III |
| Purple Color Family | | | |
| 5.5 | 0.282 | 0.200 | III |
| 4.4 | 0.277 | 0.205 | III |
| 12.2 | 0.292 | 0.236 | III |
| 33.0 | 0.288 | 0.266 | II |
| 9.4 | 0.285 | 0.209 | I |
| 40.1 | 0.322 | 0.286 | IV |
| 15.5 | 0.355 | 0.241 | IV |
| 3.3 | 0.285 | 0.247 | III |
| 11.3 | 0.260 | 0.232 | II |
| Blue Color Family | | | |
| 61.5 | 0.301 | 0.320 | IV |
| 18.0 | 0.245 | 0.242 | I |
| 9.0 | 0.226 | 0.222 | I |
| 4.2 | 0.237 | 0.223 | I |
| 2.3 | 0.278 | 0.260 | II |
| 47.1 | 0.281 | 0.300 | II |
| 38.4 | 0.260 | 0.289 | II |
| 26.8 | 0.247 | 0.257 | II |
| 21.6 | 0.248 | 0.248 | I |
| 10.6 | 0.271 | 0.279 | II |
| 5.4 | 0.267 | 0.266 | II |
| 8.3 | 0.253 | 0.267 | II |
| 3.6 | 0.240 | 0.254 | II |
| 4.9 | 0.258 | 0.249 | I |
| 35.4 | 0.229 | 0.288 | III |
| 26.9 | 0.233 | 0.259 | II |
| 7.6 | 0.193 | 0.187 | I |
| 38.0 | 0.266 | 0.309 | IV |
| 23.1 | 0.240 | 0.330 | IV |
| 10.3 | 0.216 | 0.281 | III |
| Green Color Family | | | |
| 15.8 | 0.255 | 0.433 | III |
| 5.0 | 0.256 | 0.356 | I |
| 48.3 | 0.303 | 0.398 | II |
| 47.4 | 0.282 | 0.371 | II |
| 25.1 | 0.252 | 0.397 | II |
| 52.2 | 0.337 | 0.478 | IV |
| 54.2 | 0.328 | 0.432 | III |
| 59.0 | 0.336 | 0.416 | III |
| 15.3 | 0.364 | 0.425 | III |
| 18.5 | 0.275 | 0.362 | II |
| 13.1 | 0.269 | 0.437 | III |
| 3.4 | 0.275 | 0.337 | I |
| White Color Family | | | |
| 67.9 | 0.334 | 0.351 | IV |
| 73.0 | 0.313 | 0.329 | I |
| 74.1 | 0.332 | 0.352 | IV |
| Grey Color Family | | | |
| 44.7 | 0.314 | 0.329 | I |
| 45.1 | 0.317 | 0.329 | I |
| 42.6 | 0.311 | 0.332 | II |
| 32.6 | 0.313 | 0.328 | I |
| 16.1 | 0.315 | 0.329 | I |
| 52.6 | 0.313 | 0.333 | II |
| 55.5 | 0.313 | 0.327 | I |
| Black Color Family | | | |
| 4.3 | 0.291 | 0.290 | I |
| 2.7 | 0.285 | 0.275 | I |
| 2.1 | 0.299 | 0.295 | I |
| 3.3 | 0.298 | 0.312 | I |
| 3.6 | 0.308 | 0.316 | I |

TABLE II

| | Spectral Reflectances and Color Coordinates | | | |
|---|---|---|---|---|
| Wavelength, nm | Skin standard | Formulation | Tile, correct | Tile adjusted |
| 400 | 19.03 | 20.70 | 21.51 | 16.67 |
| 420 | 18.96 | 20.69 | 21.10 | 16.93 |
| 440 | 21.53 | 21.68 | 20.99 | 17.65 |
| 460 | 25.35 | 24.43 | 23.27 | 20.56 |
| 480 | 28.06 | 28.30 | 27.82 | 25.67 |
| 500 | 30.13 | 30.77 | 29.03 | 27.94 |
| 520 | 31.19 | 31.31 | 29.38 | 28.24 |
| 540 | 30.01 | 30.84 | 28.48 | 27.59 |
| 560 | 31.41 | 30.76 | 28.22 | 27.33 |
| 580 | 32.85 | 34.01 | 31.49 | 30.12 |
| 600 | 44.37 | 43.54 | 42.58 | 40.52 |
| 620 | 51.24 | 51.57 | 51.27 | 47.93 |
| 640 | 54.56 | 55.09 | 55.56 | 51.10 |
| 660 | 57.09 | 57.60 | 59.22 | 53.82 |
| 680 | 58.67 | 60.41 | 61.82 | 56.55 |
| 700 | 59.95 | 62.69 | 63.93 | 58.87 |
| X | 37.14 | 37.28 | 36.14 | 33.76 |
| Y | 34.66 | 34.89 | 33.07 | 31.53 |
| Z | 28.50 | 28.54 | 27.63 | 24.20 |
| x | 0.3703 | 0.3702 | 0.3732 | 0.3732 |
| y | 0.3456 | 0.3464 | 0.3415 | 0.3523 |
| L | 58.87 | 59.07 | 57.51 | 56.15 |
| a | 9.31 | 9.02 | 11.54 | 9.05 |
| b | 12.51 | 12.70 | 11.77 | 13.75 |

From the fabric colors studied, the 117 colors of Table I, it appears that characteristics of colors compatible with the four skin color categories identified above can be identified. From these instrumentally derived color coordinates, rules were derived for obtaining compatible skin color categories that agree with the categories assigned subjectively by those skilled in the art.

It has been found that Hunter b is also satisfactory for assigning compatible skin color categories to a wider range of colors than just those of the skin, as long as these colors are in the color families described by the common terms yellow, gold, orange, red, or white. For colors of fabric or other types of objects (excluding skin and cosmetics) in families other than yellow, gold, orange, red and white, b alone does not provide enough information to assign compatible categories correctly, nor do any of the other color coordinates defined by the CIE or otherwise described in the literature. Several new color coordinates were therefore devised and found suitable for this purpose. They are modifications of the Hunter L, a, and b coordinates, based by analogy on similar coordinates defined by the CIE in 1976. They are:

Hunter hue angle $h_H$: $h_H = \tan^{-1}(b/a)$ where $\tan^{-1}$ stands for the arctangent function;
Hunter chroma $C_H$: $C_H = (a^2 + b^2)^{\frac{1}{2}}$
Hunter saturation $s_H$: $s_H = 100\, C_H/L$
(where the factor of 100 has been introduced to make the range of numerical values of $s_H$ the same order of magnitude as those of the other variables).

Hue angle is a measure, in degrees, of the position of the color in the familiar hue circle, whose major color families are, in order, red, orange, yellow, green, blue, and purple. In the Hunter and CIE systems, these are arranged in counterclockwise order starting with red on the right, with Hunter hue angles from near zero to about 30°. Oranges have $h_H$ between 30° and 60°, yellows up to about 120°, greens to about 180°, blues to about 300°, and purples between 300° and 360° (which is the same as 0°).

Chroma is a measure of the "intensity" of a color that is valid for any color family in the same way that Hunter b is for the pure yellow colors described above. Chroma can be thought of as the distance, on a color chart, between the color in question and a grey of the same lightness.

Saturation is similar to chroma in that it describes the "intensity" of color, but it is modified to account for the effect of changing lightness on this perception. Purists in colorimetry would say that saturation should not be defined in the Hunter system, but it has been found to be a useful concept even if it does not meet the strict mathematical criteria of the CIE definition.

In the following, for non-skin matter other than cosmetics, the characteristics that appear to lead to compatibility are described for each color family represented in the colors studied; all major families are included. Again the exemplary four category system is used. The discussion applies to colored objects that are not fluorescent. Fluorescence may result in departure from the described results and conclusions. The color family is first briefly described, and the rules for assigning color categories are then presented for that family. The discussion starts with the yellow family and proceeds clockwise around the color circle so as to start with simple cases and progress to more complex ones. The fabric colors have been grouped into categories (I - IV) that correspond to the categories of skin color with which they are compatible.

Yellow

The family of yellow colors, including golds, is categorized by use of the Hunter coordinate b. The limits on b for the various categories are:
I - b less than 19
II - b between 19 and 25
III - b between 25 and 40
IV - b greater than 40.

Orange

The orange family is limited to light colors of relatively high chroma, as lower chroma colors are recognized as beige, if light, or brown, if dark. There are only categories III and IV represented in the orange family. Hunter b suffices to categorize these colors:
III - b less than 28

IV - b greater than 28.

Red

Despite the fact that these colors deviate markedly from the yellow-blue axis of Hunter space by having positive values of a, the coordinate b still suffices to categorize them:
I - b less than 9
II - b between 9 and 15
III - b between 15 and 20
IV - b greater than 20.

Beige

This family includes light colors with lower saturation or chroma than the yellows. Their hue angles are near 95°. There are no category I colors in this family. The beiges are categorized by Hunter saturation $s_H$ as follows:
II - $s_H$ less than 25
III - $s_H$ between 25 and 28
IV - $s_H$ greater than 28.

Brown

The brown family is slightly redder and significantly darker than the beige. Its hue angle is near 60°. It is best categorized by Hunter chroma $C_H$, as follows:
I - $C_H$ less than 5
II - $C_H$ between 5 and 9.5
III - $C_H$ between 9.5 and 12
IV - $C_H$ greater than 12.

Pink

This color family is difficult to categorize because it includes both yellowish pinks (peaches) and purplish pinks. These two may be distinguished by different ranges of Hunter b. The yellowish pinks include the category III and category IV colors, and these are separated by their different lightness levels. The purplish pinks include the category II and category I colors, and these are separated by their different saturations. The rules are:
I - b less than 15 and $s_H$ greater than 60
II - b less than 15 and $s_H$ less than 60
III - b greater than 15 and L less than 60
IV - b greater than 15 and L greater than 60.

Purple

This color family encompasses a wide range of hue angles. Both this quantity and the saturation $s_H$ must be considered to define the categories involved. The rules are:
I - $s_H$ less than 70 and $h_H$ less than 320°
II - $s_H$ between 50 and 70 and $h_H$ less than 320°
III - $s_H$ between 50 and 60 if $h_H$ less than 320° and $s_H$ greater than 50 if $h_H$ greater than 320°
IV - $s_H$ less than 50, with no restriction on $h_H$.

Blue

The colors in the blue family cover a wide range of hue angles, and this quantity has a major effect on their category. Together with restrictions on Hunter b, they can be categorized as follows. Note that values of Hunter b are negative, characteristic of blue rather than yellow colors. In this context, "less than" means more negative and "greater than" means less negative. The rules are:
I - b less than −10 and $h_H$ greater than 270°
II - b greater than −10 for $h_H$ greater than 270° and b less than −8.5 for $h_H$ between 270° and 230°
III - b less than −8 and $h_H$ between 230° and 210°
IV - b greater than −8 and $h_H$ less than 210°.

Green

The green family is also complex, including both bluish and yellow colors. To define the categories within this family, a variety of color coordinates must be specified:
I - $h_H$ greater than 170°
II - $h_H$ between 140° and 170° and $s_H$ less than 70
III - s greater than 70 for $h_H$ greater than 140°; no restriction on $s_H$ for $h_H$ less than 140°
IV - b greater than 30.

White

Although white fabric colors of category I exist, with values of Hunter b less than approximately 5, none was included among the samples tested. Likewise, the limits for categories III and IV are not fully defined. Tentative limits are:
I - b less than 5
II - b between 5 and 10
III or IV - b greater than 10.

Grey

This family consists of relatively light greys, all falling in categories I or II. They are best differentiated by saturation, which is always quite small for these near-neutral colors:
I - $s_H$ less than 8
II - $s_H$ greater than 8.

Black

All blacks, which include very dark greys, are in the category I. The family can be defined by upper limits on its saturation and lightness:
I - $s_H$ less than 30 and L less than 25.

Cosmetics

In a similar study of cosmetic colors, the same exemplary four color categories were used. Again, the characteristics of colors compatible with these skin color categories can be identified and rules can be derived from the instrumentally measured color coordinates for obtaining compatible skin color categories that agree with the categories assigned subjectively by those skilled in the art.

In the following, the categories that lead to compatibility for cosmetic colors are given for the same color families described above. The same limitation to nonfluorescent colors applies. For cosmetic colors, the characteristic Hunter b suffices to establish the major boundary separating categories I and II from categories III and IV. In most color families, for cosmetic colors, it is desirable to define the remaining two boundaries, between categories I and II and between categories III and IV, in an overlapping fashion to allow for the effect of widely differing skin colors. The second color family considered, Red and Orange, provides an example of this practice.

Yellow

The small number of cosmetics in the yellow color family, which also includes golds and related colors, allows establishment of the major boundary separating categories I and II from categories III and IV at b=12.5, but does not allow estimation of the boundaries between categories I and II and between categories III and IV.

Red and Orange

It is expedient to consider these two colors as a single color family. For these colors, the major boundary separating categories I and II from categories III and IV occurs at b=9.5. The boundary between categories I and II normally occurs at b=5.0, but when considering many of the darker skin colors, for example, the upper boundary of category I can be higher as required, but cannot exceed the upper boundary of category II, b=9.5. Similarly, the boundary between categories III and IV normally occurs at b=12.8, but when considering skin colors of many persons of a Hispanic background, for example, the upper boundary of category III can be higher as required. These statements can be summarized by the following mathematical equations:

I - b≦9.5

II - 5.0<b≦9.5

III - b>9.5

IV - b>12.8.

where the signs < ("less than"), ≦("less than or equal to"), >("greater than"), and ≧("greater than or equal to"), have their usual mathematical meanings. This abbreviated form of the description is used where appropriate in the following descriptions of color families and their categories.

Beige and Brown

It is convenient to combine these two similar color families. The categories are described by the following values of Hunter b:
I—b≦7.6
II—4.6<b≦7.6
III—b>7.6
IV—b≧9.6.

Pink

This color family includes such colors as peach. The categories are described by the following values of Hunter b:
I—b≦9.5
II—2.4<b≦9.5
III—b>9.5
IV—b≧11.8.

Purple

Included in the purple family are violet, lavender, and similar colors. The majority of these colors fall in categories I and II. The description of these categories in terms of Hunter b is as follows:

I—b≦5.6

II—14.5<b≦5.6.

An exceptional case occurs, for reasons not now known to us, when for a color in this family Hunter L≦30, a≦10, and b≦−25. In such a case, visual inspection shows that the color is compatible with skin colors in category III.

Blue

The category boundaries for this color family in terms of Hunter b are as follows:
I—b≦−14.5
II—18.8<b≦−14.5
III—b>−−14.5
IV—b≧−1.8.

Green

The category boundaries for this color family can be established in terms of Hunter b as follows:
I—b≦−1.8
II—−3.1<b≦−1.8
III—b>1.8
IV—b≧4.9.

White

The very small number of white cosmetics allows only the definition of the major boundary separating categories I and II from categories III and IV. This occurs at Hunter b=6.0.

Grey

Grey cosmetics are all in categories I or II, with Hunter b<1.0. It is not possible to define the boundary between these categories.

Black

As with the grey family, the black cosmetics are all in categories I and II, with Hunter b<0. It is not possible to establish the boundary between these categories.

Foundation Colors

The above rules apply to all cosmetic colors except for the brown or beige foundation colors. The selection of these colors depends not only on Hunter b, but also on the lightness of the skin color to which the foundation is to be applied, as measured by Hunter L, according to the following:
Dark skin, L<40
Medium dark skin, L<50
Medium skin, L<59
Light skin, L≧59.
Within these skin-lightness categories, it is possible to establish the boundary separating categories I and II from categories III and IV at the following values of Hunter b:
Dark skin, b=12.0
Medium dark skin, b=12.3
Medium skin, b=12.5
Light skin, b=12.8.

An instrument, having the same general configuration as that of FIG. 1, for carrying out this process can make the initial choice of family (via software) based on measurement, or can have family designation input by the operator to control the subsequent measuring, calculating, comparing and assigning steps effected by easily accomplished programming choosing comparison subroutines based on color family either input manually or measured.

The necessary measurements are made and calculations of the appropriate characteristics are carried out by the CPU. Comparison with stored ranges of characteristics for the identified family are made and a category (or categories) I-IV is assigned signifying compatibility with a like-identified skin color category.

When new product colors are formulated, the foregoing measurable characteristics can be used to arrive at colors compatible with each category of skin coloration. A particular color family can thus be represented for each category of skin coloration. In clothing, cosmetics, and accessories each prospective consumer can be assured of a selection of colors compatible with their skin color. Similar product colors can also be made available to persons of differing skin color categories. For each color family the correction of a particular color to bring it into one or another of the categories that correspond to skin color categories can be achieved by altering the formulation. In other words, adding or subtracting blue or yellow can move a product's classification to a desired category. In the art, correction of blue or yellow is achieved by appropriate adjustment of a blue or yellow content adjusting colorant of the original formulation. Repeated measurements of the parameters identified above for the various color families will confirm proper color correction for a particular classification or will indicate the need for additional correction. Correct representation of colors of products in printed advertising can be achieved in this way and printed color charts accurately reproducing product colors for such products as apparel and cosmetics can be achieved, whereas previously printed representations of product colors were very often inaccurate.

Figure 4:
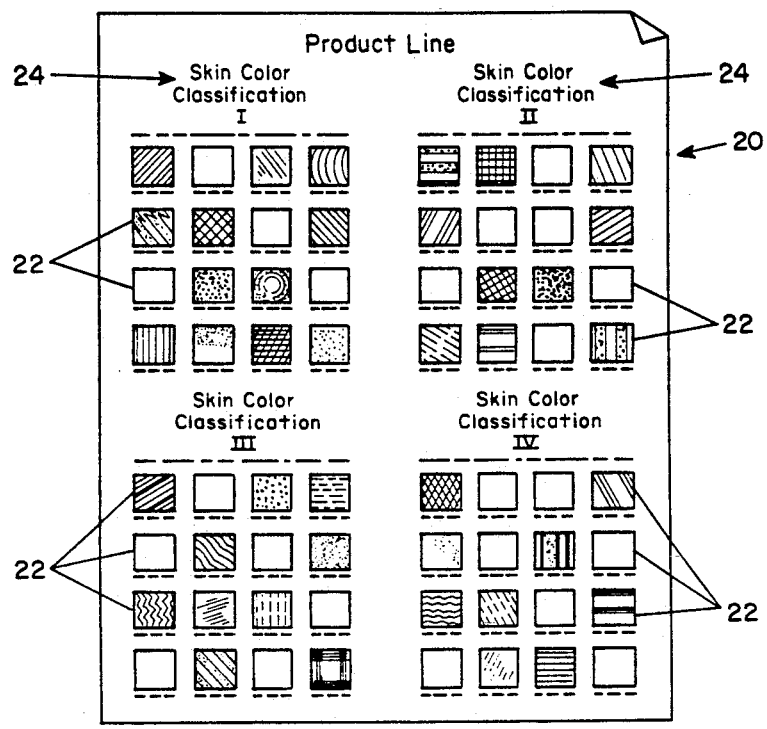
FIG. 4 is an illustration of a product color chart with product color representations brought together into regions associated with designations of skin color compatibility.
Figure 5:
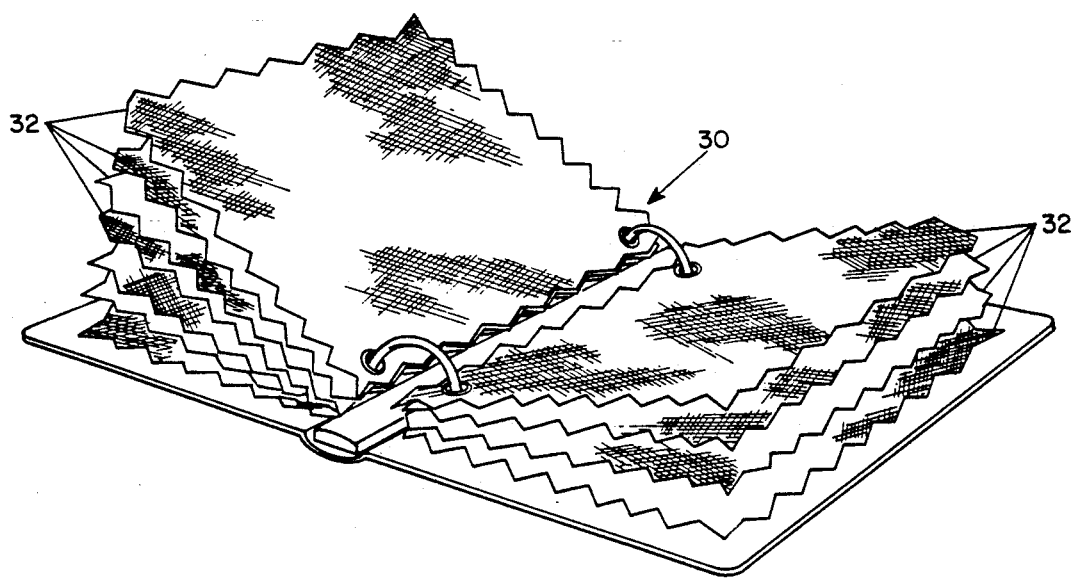
FIG. 5 is a perspective view illustrating a swatch pack of fabric samples that are assembled together for their compatibility with one of a number of skin color classifications.
Figure 6:
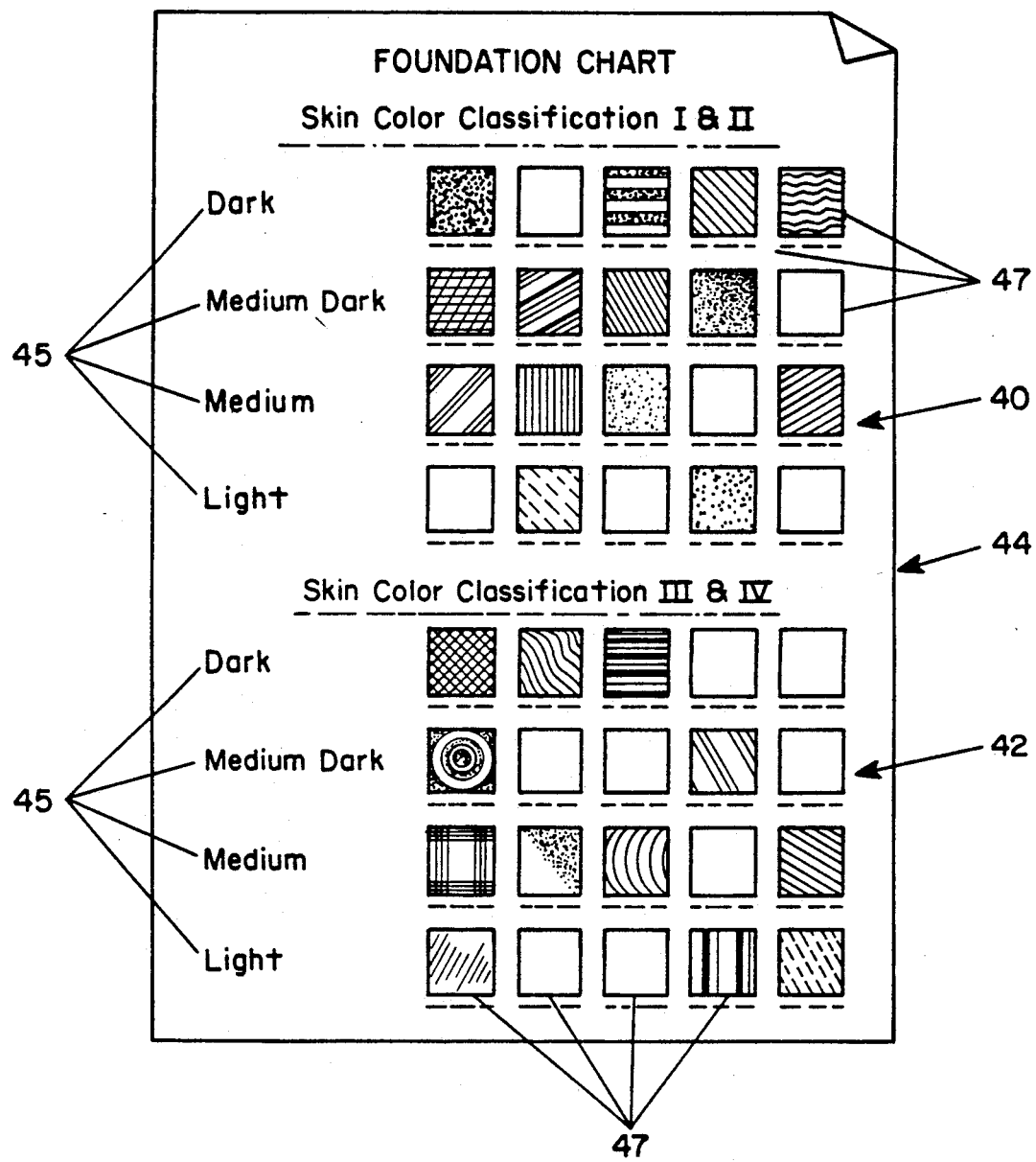
FIG. 6 is an illustration of a foundation cosmetic product color chart with beige and brown product color representations arranged for skin color compatibility as well as for skin darkness that must be taken into account.

Color charts can be accurately assembled for other than cosmetics and for cosmetics. As indicated by the chart 20 in FIG. 4, product colors gathered together in association with their compatible skin color categories can be accurately assembled by adjusting color representations 22 associated with each skin color category designation 24 in conformance with the ranges described above for each color family. Of course, each product color representation 22 can be labeled by a color designating product color name or number. For cosmetics and for products other than cosmetics the colors are assembled and classified based on four classifications of skin coloration as described above. Shown in FIG. 5, swatch packs 30 of colored fabric samples 32, correctly colored for a particular skin coloration, should gather together samples with fabric colorings as established above. Similarly, beige and brown foundation colors are assembled and classified, either on the same cosmetic color charts, or on separate charts, based on skin darkness as well as skin color classification, again as described above. In FIG. 6, two regions 40 and 42 of a foundation cosmetic color chart 44 are broken down by skin darkness categories 45 based on the Hunter L values described above. The chips or representations 47 accurately portraying the brown and beige foundation colors are then formulated and arranged to accurately identify the classifications of these products.

The above specific preferred embodiments of the invention are illustrative and may be modified as will be readily understood by those skilled in the art without departure from the spirit and scope of the invention, as set out in the appended claims.

We claim:

1. The process of identifying skin color categories for compatibility with colors of non-skin materials based on skin color undertones of an individual person including the steps of determining the value of a yellow-blue factor of the skin color of the individual person using a color measuring device, the yellow-blue factor comprising a first function weighted in a first portion of the spectrum, a second function weighted in a second portion of the spectrum, and a weighting term that is a function of the lightness of the color and that decreases the value of the yellow-blue factor with increasing lightness, classifying the skin color of the individual person into one of plural categories of skin color in dependence upon the location of the determined value in one of plural value numerical ranges defining said categories, and selecting as compatible with the skin color of the individual person one or more preselected colors assigned to said categories.

2. The process according to claim 1, wherein the first function has maximum weighting in the yellow to red region of the spectrum, and the second function has maximum weighting in substantially the blue region of the spectrum.

3. The process according to claim 2, wherein the yellow-blue factor is the difference between the first function and the second function, weighted by the term that is the function of the lightness of the skin color.

4. The process according to claim 3, wherein the yellow-blue factor is Hunter b.

5. The process according to claim 4, wherein the step of determining the Hunter b value includes measuring first Y and Z, then calculating said Hunter b value using a tristimulus colorimeter.

6. The process according to claim 4, wherein the step of classifying the skin color comprises storing the Hunter b value numerical ranges in computer memory, generating a signal representative of the Hunter b value of the individual person's skin color, electrically comparing the signal representative of the Hunter b value of the individual person's skin color with the ranges stored in memory and generating an output representative of the category into which the individual person's skin color falls.

7. The process according to claim 6, wherein the step of determining the Hunter b value of the skin color of the individual person comprises calculating an average value from a number of determinations of the person's skin color Hunter b value.

8. The process of claim 4, wherein the step of determining includes measuring skin color characteristics at the person's cheek, the step of classifying the skin color of the individual person into one of plural categories of skin color comprises comparing the Hunter b value of the person's skin at the cheek with four ranges of values having boundary values substantially as follows: 11.2, 12.7 and 14.3, said ranges corresponding to four categories of skin color.

9. The process of claim 4, wherein the step of determining includes measuring skin color characteristics at the back of the person's hand, the step of classifying the skin color of the individual person into one of the plural categories of skin color comprises comparing the Hunter b value of the person's skin color at the back of the hand with four ranges of values having boundary values substantially as follows: 9.8, 11.0 and 12.1, said ranges corresponding to four categories of skin color.

10. An instrument for identifying skin color categories compatible with particular sets of colors including means for determining the value of a yellow-blue factor of an individual person's skin color, the yellow-blue factor comprising a first function weighted in a first portion of the spectrum, a second function weighted in a second portion of the spectrum, and a weighting term that is a function of the lightness of the color and that decreases the value of the yellow-blue factor with increasing lightness, means for storing plural predetermined ranges of the yellow-blue factor values corresponding to plural skin color categories, means for comparing the determined yellow-blue factor value of the individual person's skin color to the stored ranges, and means for producing an output indicative of the category corresponding to the stored range wherein the determined value lies.

11. The instrument according to claim 10, wherein the first function has maximum weighting in substantially the yellow to red region of the spectrum, and the second function has maximum weighting in substantially the blue region of the spectrum.

12. The instrument according to claim 11, wherein the yellow-blue factor is the difference between the first function and the second function, weighted by the term that is the function of the lightness of the skin color.

13. The instrument according to claim 1 wherein the yellow-blue factor is Hunter b.

14. The instrument according to claim 13, wherein the means for determining the Hunter b value is a tristimulus colorimeter.

15. The instrument according to claim 13, wherein the stored ranges of Hunter b values are the four ranges of values having boundaries substantially as follows: 11.2, 12.7 and 14.3, representing the boundaries of categories of skin color measured at the cheek.

16. The instrument according to claim 13, wherein the stored ranges of Hunter b values are the four ranges of values having boundaries substantially as follows: 9.8, 11.0, and 12.1, representing the boundaries of categories of skin color measured at the back of the hand.

17. The process of determining color compatibility in non-skin matter with one or more categories of skin color including identifying the color family of the matter, selecting at least one color characteristic predetermined to determine compatibility in the identified color family of the non-skin matter, measuring color values of the non-skin matter, calculating the at least one characteristic from the measured values, comparing the at least one characteristic with predetermined ranges of that characteristic corresponding to colors in that family of colors compatible with one or more of the categories of skin color.

18. The process according to claim 17, wherein the color of the non-skin matter is in one of the color families yellow, orange, red and white and the characteristic establishing compatibility with skin color categories is Hunter b.

19. The process according to claim 17, wherein the non-skin matter is other than a cosmetic, the color of the non-skin matter is in one of the color families beige and gray and the characteristic establishing compatibility with skin color categories is Hunter saturation $s_H$.

20. The process according to claim 17, wherein the non-skin matter is other than a cosmetic, the color of the non-skin matter is in the color family brown and the characteristic establishing compatibility with skin color categories is Hunter chroma $C_H$.

21. The process according to claim 17, wherein the non-skin matter is other than a cosmetic, the color of the non-skin matter is in the color family pink and the characteristics establishing compatibility with skin color categories are Hunter b and Hunter saturation $s_H$ for a first two of four skin color categories, and Hunter b and lightness coordinate L for a second two of the four skin color categories.

22. The process according to claim 17, wherein the non-skin matter is other than a cosmetic, the color of the non-skin matter is in the color family purple and the characteristics establishing compatibility with skin color categories are Hunter saturation $s_H$ and Hunter hue angle $h_H$.

23. The process according to claim 17, wherein the non-skin matter is other than a cosmetic, the color of the non-skin matter is in the color family blue and the characteristics establishing compatibility with skin color categories are Hunter b and Hunter hue angle $h_H$.

24. The process according to claim 17, wherein the non-skin matter is other than a cosmetic, the color of the non-skin matter is in the color family green, the characteristics establishing compatibility with skin color categories is Hunter hue angle $h_H$ for a first of four skin color categories, are the Hunter hue angle $h_H$ and Hunter saturation $s_H$ for two further of the four skin color categories, and is Hunter b for the final of the four skin color categories.

25. The process according to claim 17, wherein the non-skin matter is other than a cosmetic, the color of the non-skin matter is in the color family black and is assigned compatibility to a first skin color category based on Hunter saturation $s_H$ and lightness L.

26. The process according to claim 17, wherein the non-skin matter is a cosmetic and the characteristic establishing compatibility with skin color is Hunter b.

27. The process according to claim 17 wherein the non-skin matter is a beige or brown foundation cosmetic, further comprising the steps of providing a number of the predetermined ranges of the characteristic dependent on skin darkness categories, and assigning to the non-skin matter at least one of the skin darkness categories and at least one of the categories of skin color based on the predetermined ranges.

28. The process according to claim 27 wherein the non-skin matter color characteristic whose ranges determine compatibility with skin color is Hunter b.

29. An instrument for determining color compatibility in non-skin matter with one or more categories of skin color including a color measuring device, a central processing unit, memory, output means for indicating the one or more compatible categories of skin color, and means for identifying the family of colors of the object, said central processing unit including means for selecting at least one characteristic of the matter's color in dependence upon the family identified by the color family identifying means, means for calculating the at least one selected characteristic, and means for comparing the calculated selected characteristic with ranges of that characteristic corresponding to one or more compatible skin color categories.

30. A method of identifying compatible skin and non-skin matter colors including assigning categories of skin coloration based on ranges of values of a yellow-blue factor of skin color, the yellow-blue factor comprising a first function weighted in a first portion of the spectrum, a second function weighted in a second portion of the spectrum and a weighting function of the lightness of the color that decreases the value of the yellow-blue factor with increasing lightness, determining skin coloration ranges based upon the yellow-blue factor for compatibility with non-skin matter, and assigning non-skin matters to categories of colors of non-skin matter, each compatible to one of the skin coloration categories, based on ranges of at least one objectively ascertainable color factor.

31. The method according to claim 30 further comprising the steps of coloring with a formulation at least one non-skin matter for compatibility with the one of the skin coloration categories including adjusting the content of a yellow or a blue color adjusting constituent in the formulation.

32. The method according to claim 31 wherein the non-skin matter is a representation of a product color.

33. The process of identifying skin color categories for compatibility with colors of non-skin materials including the steps of determining at least one boundary between at least one category greater in yellow content and at least one category greater in blue content of skin coloration, storing in computer memory a color measurement factor value defining the boundary, measuring the value of said factor for skin coloration of an individual person based at least in part on yellow and blue content of said coloration, assigning to the individual person a skin color category in dependence upon the relationship of the measured value of skin coloration with respect to the boundary defining value.

34. The process of identifying skin color categories according to claim 33 wherein increasing values of skin coloration above the value defining at least one boundary are representative of colors of increasingly yellow content, and decreasing values of skin coloration below the value defining the boundary are representative of colors of increasingly blue content.

35. The process according to claim 34 wherein the value defining the boundary is the value of a yellow-blue factor comprising a first function weighted in the yellow portion of the spectrum, a second function weighted in the blue portion of the spectrum, and a weighting term that is a function of the lightness of the color and that decreases the value of the yellow-blue factor with increasing lightness.

36. The process according to claim 35 wherein the yellow-blue factor is Hunter b.

37. The process according to claim 36 wherein the value defining the boundary is a Hunter b value of substantially 12.7 for measurements at the cheek of an individual.

38. The process according to claim 36 wherein the value of the at least one boundary is a Hunter b value of substantially 11.0 for measurements at the hand of an individual.

39. The process according to claim 33 further comprising the steps of determining further boundaries dividing in two the regions of coloration on either side of the at least one boundary, storing in memory the further boundaries, and the step of assigning to the individual person a skin color category further including determining the location of the measured value of skin coloration with respect to said further boundaries.

40. The process of identifying the skin color categories of an individual comprising the steps of measuring and establishing skin coloration categories based on blue and yellow content, including providing at least one boundary dividing an increasingly yellow content of skin coloration region from an increasing blue content region, measuring by instrument at least one skin coloration characteristic value of an individual person sufficient to locate the skin coloration of the individual in one of the categories thus established.

41. The skin coloration identification process according to claim 40 wherein the step of providing at least one boundary includes providing a central boundary measure between yellower and bluer regions of skin coloration, the boundary having a color value corresponding to particular, predetermined value of Huntter b.

42. The skin coloration identification process according to claim 41 wherein the particular value of Hunter b varies with the location of measurement of skin coloration on the individual person and is in the range of Hunter b from substantially 11.0 to substantially 12.7.

43. The skin coloration identification process according to claim 40 further comprising the steps of providing at least two further boundaries to establish on the basis of blue and yellow content at least four ranges of measurable values of skin coloration, and further comprising the step of assigning skin coloration to one of the ranges thereby enabling identification on the basis of the skin coloration assignment, of color compatible non-skin matter.

44. An instrument for identifying skin coloration categories based on blue and yellow content comprising means for retaining identification of at least one boundary between skin coloration categories dividing regions increasingly yellow in skin color content and increasingly blue in skin color content, means for measuring an individual person's skin coloration based on blue and yellow content, and means for assigning the measured coloration of an individual person's skin to a category defined by the means for retaining boundary identification.

45. The instrument according to claim 44 wherein the means for retaining boundary identification comprises means storing at least a color value central between yellower and bluer regions of skin coloration and corresponding to a particular, predetermined value of Hunter b.

46. The instrument according to claim 45 wherein the value of Hunter b is a value in the range from substantially 11.0 to substantially 12.7, and that resides at a single value in said range in dependence on the location of the measurement on the individual person.

47. The instrument according to claim 44 wherein the means for retaining boundary identification comprises means storing at least two further boundaries to establish on the basis of blue and yellow content at least four ranges of measurable values of skin coloration, and said means for assigning the measured coloration of an individual person's skin to a category being a means for assigning the measured coloration to one of at least four categories delineated by the boundaries.

48. The process of providing color compatibility in non-skin matter with one or more categories of skin color including identifying the color family desired for the matter, selecting at least one color characteristic predetermined to determine compatibility in the identified color family of the non-skin matter, measuring color values of a coloring formulation of the non-skin matter, calculating the at least one characteristic from the measured values, comparing the at least one characteristic with a predetermined range of that characteristic corresponding to colors in that family of colors compatible with one or more of the categories of skin color, and when the at least one characteristic is outside of the predetermined range, adjusting the content of a blue or yellow color adjusting constituent in the coloring formulation until the at least one color characteristic is in the predetermined range.

49. The method of determining a coloring formulation for a non-skin matter including providing color compatibility categories exclusively on the basis of skin color content in the bluer and yellower regions of the spectrum, providing in the formulation an amount of at least one of a constituent colorant sufficient to place non-skin matter colored by the coloring formulation in a range of at least one characteristic predetermined to effect compatibility of the non-skin matter color and at least one desired category of skin color.

50. The method of determining a color formulation according to claim 49 wherein the constituent colorant is a blue content contributing constituent of the coloring formulation.

51. The method of determining a color formulation according to claim 49 wherein the constituent colorant is a yellow content contributing constituent of the coloring formulation.

52. The method of determining a color formulation according to claim 49 wherein the non-skin matter is a printed color representation.

53. The method of determining a color formulation according to claim 52 wherein the printed color representation is a color chart representative of a line of product colors.

54. The method of determining a color formulation according to claim 49 wherein the non-skin matter is a cosmetic.

55. The method of determining a color formulation according to claim 49 the non-skin matter is a fabric.

56. A color chart having a region associated with one category of skin coloration and including representations of at least a plurality of the following colors: yellow with a Hunter b less than 19, red with a Hunter b less than 9, brown with a Hunter chroma $C_H$ less than 5, pink with a Hunter b less than 15 and a Hunter saturation $s_H$ greater than 60, purple with a Hunter saturation $s_H$ less than 70 and a Hunter hue angle $h_H$ less than 320°, blue with a Hunter b less than $-10$ and a Hunter hue angle $h_H$ greater than 270°, green with a Hunter hue angle $h_H$ greater than 170°, white with a Hunter b less than 5, grey with a Hunter saturation $s_H$ less than 8, and black.

57. A color chart having a region associated with one category of skin coloration and including representations of at least a plurality of the following colors: yellow with a Hunter b between 19 and 25, red with a Hunter b between 9 and 15, beige with a Hunter saturation $s_H$ less than 25, brown with a Hunter chroma $C_H$ between 5 and 9.5, pink with a Hunter b less than 15 and a Hunter saturation $s_H$ less than 60, purple with a Hunter saturation $s_H$ between 50 and 70 and a Hunter hue angle $h_H$ less than 320°, blue with a Hunter b greater than $-10$ for a Hunter hue angle $h_H$ greater than 270° and less than $-8.5$ for a Hunter hue angle $h_H$ between 270° and 230°, green with a Hunter hue angle $h_H$ between 140° and 170° and Hunter saturation $s_H$ less than 70, white with a Hunter b between 5 and 10, grey with a Hunter saturation $s_H$ greater than 8.

58. A color chart having a region associated with one category of skin coloration and including representations of at least a plurality of the following colors: yellow with a Hunter b between 25 and 40, orange with a Hunter b less than 28, red with a Hunter b between 15 and 20, beige with a Hunter saturation $s_H$ between 25 and 28, brown with a Hunter chroma $C_H$ between 9.5 and 12, pink with a Hunter b greater than 15 and a Hunter L less than 60, purple with a Hunter saturation $s_H$ between 50 and 60 if Hunter hue angle $s_H$ is less than 320° and greater than 50 if Hunter hue angle $h_H$ is greater than 320°, blue with a Hunter b greater than $-8$ and a Hunter hue angle $h_H$ between 230° and 210°, green with a Hunter saturation $s_H$ greater than 700 for a Hunter hue angle $h_H$ greater than 140° and no restriction on Hunter saturation $s_H$ for Hunter hue angle $h_H$ less than 140°, white with a Hunter b greater than 10.

59. A color chart having a region associated with one category of skin coloration and including representations of at least a plurality of the following colors: yellow with a Hunter b greater than 40, orange with a Hunter b greater than 28, red with a Hunter b greater than 20, beige with a Hunter saturation $s_H$ greater than 28, brown with a Hunter 15 and a Hunter L greater than 60, purple with a Hunter saturation $s_H$ less than 50 and no restriction on Hunter hue angle $h_H$, blue with a Hunter b greater than $-8$ and a Hunter hue angle $h_H$ less than 210°, green with a Hunter b greater than 30, white with a Hunter b greater than 10.

60. A swatch pack of fabric samples assembled for association with one category of skin coloration and including fabrics of at least a plurality of the following colors: yellow with a Hunter b less than 19, red with a Hunter b less than 9, brown with a Hunter chroma $C_H$ less than 5, pink with a Hunter b less than 15 and a Hunter saturation $s_H$ greater than 60, purple with a Hunter saturation $s_H$ less than 70 and a Hunter hue angle $h_H$ less than 320°, blue with a Hunter b less than $-10$ and a Hunter hue angle $h_H$ greater than 270°, green with a Hunter hue angle $h_H$ greater than 170°, white with a Hunter b less than 5, grey with a Hunter saturation $s_H$ less than 8, and black.

61. A swatch pack of fabric samples assembled for association with one category of skin coloration and including fabrics of at least a plurality of the following colors: yellow with a Hunter b between 19 and 25, red with a Hunter b between 9 and 15, beige with a Hunter saturation $s_H$ less than 25, brown with a Hunter chroma $C_H$ between 5 and 9.5, pink with a Hunter b less than 15 and a Hunter saturation $s_H$ less than 60, purple with a Hunter saturation $s_H$ between 50 and 70 and a Hunter hue angle $h_H$ less than 320°, blue with a Hunter b greater than $-10$ for a Hunter hue angle $h_H$ greater than 270° and less than $-8.5$ for a Hunter hue angle $h_H$ between 270° and 230°, green with a Hunter hue angle $h_H$ between 140° and 170° and Hunter saturation $s_H$ less than 70, white with a Hunter b between 5 and 10, grey with a Hunter saturation $s_H$ greater than 8.

62. A swatch pack of fabric samples assembled for association with one category of skin coloration and including fabrics of at least a plurality of the following colors: yellow with a Hunter b between 25 and 40, orange with a Hunter b less than 28, red with a Hunter b between 15 and 20, beige with a Hunter saturation $s_H$ between 25 and 28, brown with a Hunter chroma $C_H$ between 9.5 and 12, pink with a Hunter b greater than 15 and a Hunter L less than 60, purple with a Hunter saturation $s_H$ between 50 and 60 if Hunter hue angle $s_H$ is less than 320° and greater than 50 if Hunter hue angle $h_H$ is greater than 320°, blue with a Hunter b greater than $-8$ and a Hunter hue angle $h_H$ between 230° and 210°, green with a Hunter saturation $s_H$ greater than 70 for a Hunter hue angle $h_H$ greater than 140° and no restriction on Hunter saturation $s_H$ for Hunter hue angle $h_H$ less than 140°, white with a Hunter b greater than 10.

63. A swatch pack of fabric samples assembled for association with one category of skin coloration and including fabrics of at least a plurality of the following colors: yellow with a Hunter b greater than 40, orange with a Hunter b greater than 28, red with a Hunter b greater than 20, beige with a Hunter saturation $s_H$ greater than 28, brown with a Hunter chroma $C_H$ greater than 12, pink with a Hunter b greater than 15 and a Hunter L greater than 60, purple with a Hunter saturation $s_H$ less than 50 and no restriction on Hunter hue angle $h_H$, blue with a Hunter b greater than −8 and a Hunter hue angle $h_H$ less than 210°, green with a Hunter b greater than 30, white with a Hunter b greater than 10.

64. A cosmetic color chart having a region associated with one category of skin coloration and including representations of at least a plurality of the following colors: yellow with a Hunter b less or equal to 12.5, red with a Hunter b less than or equal to 9.5, orange with a Hunter b less than or equal to 9.5, beige with a Hunter b less than or equal to 7.6, brown with a Hunter b less than or equal to 7.6, pink with a Hunter b less than or equal to 9.5, purple with a Hunter b less than or equal to 5.6, blue with a Hunter b less than or equal to −14.5, green with a Hunter b less than or equal to −1.8, white with a Hunter b less than or equal to 6.0, grey with a Hunter b less than 1.0 and black with a Hunter b less than 0.

65. The chart according to claim 64 further comprising at least one of the following foundation colors: a brown or beige foundation color with a Hunter b less than or equal to 12.0 and designated for dark skin, a brown or beige foundation color with a Hunter b less than or equal to 12.3 designated for medium dark skin, a brown or beige foundation color with a Hunter b less than or equal to 12.5 designated for medium skin, and a brown or beige foundation color with a Hunter b less than or equal to 12.8 designated for light skin; where dark skin is skin with a Hunter L less than 40, medium dark skin is skin with a Hunter L less than 50, medium skin is skin with a Hunter L less than 59, and light skin is skin with a Hunter L greater than or equal to 59.

66. A cosmetic color chart having a region associated with one category of skin coloration and including representations of at least a plurality of the following colors: yellow with a Hunter b less than or equal to 12.5, red with a Hunter b greater than 5.0 and less than or equal to 9.5, orange with a Hunter b greater than 5.0 and less than or equal to 9.5, beige with a Hunter b greater than 4.6 and less than or equal to 7.6, brown with a Hunter b greater than 4.6 and less than or equal to 7.6, pink with a Hunter b greater than −2.4 and less than or equal to 9.5, purple with a Hunter b greater than −14.5 and less than or equal to 5.6, blue with a Hunter b greater than −18.8 and less than or equal to −14.5, green with a Hunter b greater than −3.1 and less than or equal to −1.8, white with a Hunter b less than or equal to 6.0, grey with a Hunter b less than 1.0, and black with a Hunter b less than 0.

67. The chart according to claim 66 further comprising at least one of the following foundation colors: a brown or beige foundation color with a Hunter b less than or equal to 12.0 and designated for dark skin, a brown or beige foundation color with a Hunter b less than or equal to 12.3 designated for medium dark skin, a brown or beige foundation color with a Hunter b less than or equal to 12.5 designated for medium skin, and a brown or beige foundation color with a Hunter b less than or equal to 12.8 designated for light skin; where dark skin is skin with a Hunter L less than 40, medium dark skin is skin with a Hunter L less than 50, medium skin is skin with a Hunter L less than 59, and light skin is skin with a Hunter L greater than or equal to 59.

68. A cosmetic color chart having a region associated with one category of skin coloration and including representations of at least a plurality of the following colors: yellow with a Hunter b greater than or equal to 12.5, red with a Hunter b greater than 9.5, orange with a Hunter b greater than 9.5, beige with a Hunter b greater than 7.6, brown with a Hunter b greater than 7.6, pink with a Hunter b greater than 9.5, purple with a Hunter L less than or equal to 30, a Hunter a less than or equal to 10 and a Hunter b less than or equal −25, blue with a Hunter b greater than −14.5, green with a Hunter b greater than 1.8, and white with a Hunter b greater than 6.0.

69. The chart according to claim 68 further comprising at least one of the following foundation colors: a brown or beige foundation color with a Hunter b greater than 12.0 and designated for dark skin, a brown or beige foundation color with a Hunter b greater than 12.3 designated for medium dark skin, a brown or beige foundation color with a Hunter b greater than 12.5 designated for medium skin, and a brown or beige foundation color with a Hunter b greater than 12.8 designated for light skin; where dark skin is skin with a Hunter L less than 40, medium dark skin is skin with a Hunter L less than 50, medium skin is skin with a Hunter L less than 59, and light skin is skin with a Hunter L greater than or equal to 59.

70. A cosmetic color chart having a region associated with one category of skin coloration and including representations of at least a plurality of the following colors: yellow with a Hunter b greater than or equal to 12.5, red with a Hunter b greater than or equal to 12.8, orange with a Hunter b greater than or equal to 12.8, beige with a Hunter b greater than or equal to 9.6, brown with a Hunter b greater than or equal to 9.6, pink with a Hunter b greater than or equal to 11.8, blue with a Hunter b greater than or equal to −1.8, green with a Hunter b greater than or equal to 4.9 and white with a Hunter b greater than or equal to 6.

71. The chart according to claim 70 further comprising at least one of the following foundation colors: a brown or beige foundation color with a Hunter b greater than 12.0 and designated for dark skin, a brown or beige foundation color with a Hunter b greater than 12.3 designated for medium dark skin, a brown or beige foundation color with a Hunter b greater than 12.5 designated for medium skin, and a brown or beige foundation color with a Hunter b greater than 12.8 designated for light skin; where dark skin is skin with a Hunter L less than 40, medium dark skin is skin with a Hunter L less than 50, medium skin is skin with a Hunter L less than 59, and light skin is skin with a Hunter L greater than or equal to 59.

72. A cosmetic foundation color chart having at least two regions associated with at least two skin color classification and skin darkness designations based upon Hunter L values less than 40 for a dark skin designation, less than 50 for a medium dark skin designation, less than 59 for a medium skin designation, and greater than or equal to 59 for a light skin designation, and brown and beige color representations having Hunter b less than or equal to 12 for dark skin in one of the regions and Hunter b greater than 12 for the dark skin designation in another of the regions, Hunter b less than or equal to 12.3 for the medium dark skin designation in the one region, and Hunter b greater than 12.3 for the medium dark skin designation in the other region, Hunter b less than or equal to 12.5 for the medium skin designation in the one region and Hunter b greater than 12.5 for the medium skin designation in the other region, and Hunter b less than or equal to 12.8 for the light skin designation in the one region and Hunter b greater than 12.8 for the light skin designation in the other region.

73. A method of making a color chart, having representations of colors assigned for compatibility to several categories of skin coloration encompassing the entire human community, including providing said several categories of skin coloration based exclusively upon skin color content in the bluer to yellower regions of the spectrum, and assigning each color representation to one of said categories based upon a measured color characteristic predetermined to establish compatibility of the color representation in one of the categories.

74. The method according to claim 73 wherein the step of providing categories of skin coloration includes providing a plurality of categories having at least a central boundary measure between yellower and bluer regions of skin coloration.

75. The method according to claim 74 wherein the central boundary is established in a range of Hunter b from substantially 11.0 to 12.7, in dependence upon the location of an individual person where skin color measurement is made.

76. The method according to claim 73 wherein the step of providing categories includes establishing four categories of skin coloration having boundaries at Hunter b values substantially as follows: 11.2, 12.7, and 14.3, representing the boundaries of categories of skin color measured at the cheek.

77. The method according to claim 73 wherein the step of providing categories includes establishing four categories of skin coloration having boundaries at Hunter b values substantially as follow: 9.8, 11.0, and 12.1, representing the boundaries of categories of skin color measured at the back of the hand.

78. The process of identifying skin color categories based on skin color undertones of an individual person comprising the steps of determining at least the value of a yellow-blue factor of the skin color of an individual person using a color measuring device, the yellow-blue factor comprising a first function weighted in a first portion of the spectrum, a second function weighted in a second portion of the spectrum, and a weighting term that is a function of the lightness of the color and that decreases the value of the yellow-blue factor with increasing lightness, classifying the skin color of the individual person into one of plural categories of skin color in dependence upon the location of the determined value in one of plural numerical value ranges defining said categories.

79. The process according to claim 78 wherein the step of determining includes measuring the value of Hunter b in the skin color of the individual person.

80. The processing of categorizing the color of a non-skin material, composition or item including the steps of determining at least the value of a yellow-blue factor of the color of the material, composition or item using a color measuring device, the yellow-blue factor comprising a first function weighted in a first portion of the spectrum, a second function weighted in a second portion of the spectrum, and a term that is a function of the lightness of the color and that decreases the value of the yellow-blue factor with increasing lightness, classifying the color of the non-skin material, composition, or item into one of plural categories of color in dependence upon the location of the determined value in one of plural value numerical ranges defining said categories.

81. The process according to claim 80 wherein the step of determining includes measuring the value of Hunter b in the color of the non-skin material, compositions or item.

82. The process of identifying the skin color categories of an individual comprising the steps of measuring and establishing skin coloration categories based on content of a first color and a second color, including providing at least one boundary dividing a region of increased first color content of skin coloration from a region of increased second color content of skin coloration, measuring by instrument at least one skin coloration characteristic value of an individual person sufficient to locate the skin coloration of the individual in one of the categories thus established.

83. The process according to claim 82 wherein the first and second colors are opponent colors.

84. An instrument for identifying skin coloration categories based on first color and second color content comprising means for retaining identification of at least one boundary between skin coloration categories dividing regions increasingly of the first color in skin color content and increasingly of the second color in skin color content, means for measuring an individual person's skin coloration based on the first and second color content, and means for assigning the measured coloration of an individual person's skin to a category defined by the means for retaining boundary identification.

85. The instrument according to claim 84 wherein the first and second colors are opponent colors.

86. The process of identifying skin color categories based on skin color undertones of an individual person comprising the steps of determining at least the value of a color factor dependent on the relative content of two colors in the skin color of an individual person using a color measuring device, the color factor comprising a first function weighted in a first portion of the spectrum, a second function weighted in a second portion of the spectrum, and a weighting term that is a function of the lightness of the color and that decreases the value of the color factor with increasing lightness, classifying the skin color of the individual person into one of plural categories of skin color in dependence upon the location of the determined value in one of plural numerical value ranges defining said categories.

87. The processing according to claim 86 wherein the two colors are opponent colors.

* * * * *

UNITED STATES PATENT AND TRADEMARK OFFICE
CERTIFICATE OF CORRECTION

PATENT NO. : 5,313,267
DATED : May 17, 1994
INVENTOR(S) : MacFarlane et al.

It is certified that error appears in the above-indentified patent and that said Letters Patent is hereby corrected as shown below:

Col. 3, line 23, "an y" should read --and y--;

Col. 4, lines 44-45, "character-istic" should read --characteristics--;

Col. 8, line 9, "10 (Y" should read $--10(Y)^{1/2}--$;

Col. 10, line 29, "0.260" should read --0.264--;

Col. 11, line 3, "Tile" should read --Tile,--;

Col. 14, line 13, "s greater" should read --$s_H$ greater--;

Col. 15, line 28, ">" should read --$\geq$--;

Col. 15, line 50, "2.4" should read -- -2.4 --;

UNITED STATES PATENT AND TRADEMARK OFFICE
CERTIFICATE OF CORRECTION

PATENT NO. : 5,313,267
DATED : May 17, 1994
INVENTOR(S) : MacFarlane et al.

It is certified that error appears in the above-indentified patent and that said Letters Patent is hereby corrected as shown below:

Col. 15, line 62, "14.5" should read -- -14.5 --;

Col. 16, line 6, "18.8" should read -- -18.8 --;

Col. 16, line 7, " - -14.5" should read -- -14.5--;

Col. 19, line 17, "claim 1" should read --claim 12--;

Col. 20, lines 12-13, "characteristics" should read --characteristic(s)--;

Col. 21, line 7, "The" should read --A--;

Col. 21, line 68, "particular" should read --a particular--;

Col. 22, line 64, "The" should read --A--;

Col. 23, line 24, "the" should read --wherein the--;

Col. 23, line 67, "700" should read --70--;

UNITED STATES PATENT AND TRADEMARK OFFICE
CERTIFICATE OF CORRECTION

PATENT NO. : 5,313,267
DATED : May 17, 1994
INVENTOR(S) : MacFarlane et al.

It is certified that error appears in the above-indentified patent and that said Letters Patent is hereby corrected as shown below:

Col. 24, line 9, "Hunter 15" should read --Hunter chroma $C_H$ greater than 12, pink with a Hunter b greater than 15--;

Col. 25, line 10, "less" should read --less than--;

Col. 27, line 22, "of" should read --on--;

Col. 27, line 33, "follow" should read --follows--;

Col. 27, line 54, "processing" should read --process--;

Col. 28, line 9, "value numerical" should read --numerical value--;

Col. 28, lines 13-14, "compositions" should read --composition--.

Col. 28, line 56, "processing" should read --process--.

Signed and Sealed this

Seventh Day of January, 1997

Attest:

BRUCE LEHMAN

Attesting Officer

Commissioner of Patents and Trademarks